(12) United States Patent
Weiss et al.

(10) Patent No.: US 11,684,922 B2
(45) Date of Patent: Jun. 27, 2023

(54) DEVICE AND METHOD FOR INTRACELLULAR DELIVERY OF BIOMOLECULAR CARGO VIA ACOUSTIC WAVE EXPOSURE

(71) Applicant: THE REGENTS OF THE UNIVERSITY OF CALIFORNIA, Oakland, CA (US)

(72) Inventors: Paul S. Weiss, Los Angeles, CA (US); Steven J. Jonas, Hawthorne, CA (US); Dan Wilkinson, New York, NY (US); Adam Z. Stieg, Pasadena, CA (US); Jason Belling, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 936 days.

(21) Appl. No.: 16/485,424

(22) PCT Filed: Feb. 13, 2018

(86) PCT No.: PCT/US2018/017965
§ 371 (c)(1),
(2) Date: Aug. 12, 2019

(87) PCT Pub. No.: WO2018/148715
PCT Pub. Date: Aug. 16, 2018

(65) Prior Publication Data
US 2019/0381507 A1     Dec. 19, 2019

Related U.S. Application Data

(60) Provisional application No. 62/458,289, filed on Feb. 13, 2017.

(51) Int. Cl.
*B01L 3/00*     (2006.01)
*H01L 41/08*    (2006.01)
(Continued)

(52) U.S. Cl.
CPC ........ *B01L 3/502761* (2013.01); *C12N 15/87* (2013.01); *H01L 41/04* (2013.01);
(Continued)

(58) Field of Classification Search
CPC ....... B01L 3/502761; B01L 2400/0436; B01L 2400/0442; C12N 15/87; H01L 41/04;
(Continued)

(56) References Cited

U.S. PATENT DOCUMENTS 7,500,379 B2   3/2009 Hines
7,704,743 B2   4/2010 Fedorov et al.
(Continued)

FOREIGN PATENT DOCUMENTS

JP       2014/192692      10/2014
WO       WO-0242447 A2 *  5/2002   ............ C12M 23/20
(Continued)

OTHER PUBLICATIONS

PCT International Preliminary Report on Patentability (Chapter I of the Patent Cooperation Treaty) for PCT/US2018/017965, Applicant: The Regents of the University of California, Form PCT/IB/326 and 373, dated Aug. 22, 2019 (12 pages).
(Continued)

*Primary Examiner* — Matthew D Krcha
*Assistant Examiner* — Jean Caraballo-Leon
(74) *Attorney, Agent, or Firm* — Vista IP Law Group LLP

(57) ABSTRACT

A microfluidic-based device and system is disclosed for the high-throughput intracellular delivery of biomolecular cargo to cells (eukaryotic or prokaryotic) or enveloped viruses. Cargo integration occurs due to transient membrane permeabilization by exposure to bulk acoustic waves (BAWs) transduced from surface acoustic waves (SAWs) generated by a rapidly oscillating piezoelectric substrate. In this approach, temporary pores are established across the cellular
(Continued)

membrane as cells are partially deformed and squeezed or subject to shearing forces as they travel through the vibrational modes created within the microfludic channel(s) of the device.

26 Claims, 10 Drawing Sheets

(51) Int. Cl.
  H01L 41/04 (2006.01)
  C12N 15/87 (2006.01)
(52) U.S. Cl.
  CPC ..... *H01L 41/081* (2013.01); *B01L 2400/0436* (2013.01); *B01L 2400/0442* (2013.01)
(58) Field of Classification Search
  CPC ............. H01L 41/081; C12M 23/16; G01N 2291/0423; G01N 2291/0426; G01N 29/222
  See application file for complete search history.

(56) References Cited

U.S. PATENT DOCUMENTS

| | | | |
|---|---|---|---|
| 8,334,133 B2 | 12/2012 | Fedorov et al. | |
| 9,512,421 B1 | 12/2016 | Branch et al. | |
| 2002/0009015 A1* | 1/2002 | Laugharn, Jr. .......... | B01F 35/71 366/108 |
| 2008/0156100 A1* | 7/2008 | Hines ................. | G01N 29/2481 73/584 |
| 2013/0213488 A1 | 8/2013 | Weitz et al. | |
| 2014/0014516 A1 | 1/2014 | Weiss et al. | |
| 2014/0033808 A1 | 2/2014 | Ding et al. | |
| 2014/0273229 A1 | 9/2014 | Meacham et al. | |
| 2016/0186212 A1 | 6/2016 | Lee | |

FOREIGN PATENT DOCUMENTS

| | | |
|---|---|---|
| WO | WO 2013/059343 | 8/2013 |
| WO | 2016/077761 A1 | 5/2016 |
| WO | WO 2016/077761 A1 | 5/2016 |
| WO | WO 2016/210128 | 12/2016 |
| WO | WO 2018/039084 | 3/2018 |

OTHER PUBLICATIONS

Response to extended European search report dated Feb. 23, 2022, for European Patent Application No. 21166837.1-1132, Applicant: The Regents of the University of California, (57 pages).
The extended European search report dated Jul. 26, 2021, for European Patent Application No. 21166837.1-1132, Applicant: The Regents of the University of California, (16 pages).
Communication pursuant to Rules 70(2) and 70a(2) EPC dated Aug. 30, 2021, for European Patent Application No. 21166837.1-1132, Applicant: The Regents of the University of California, (1 page).
Barani, Alireza et al., Microfluidic integrated acoustic waving for manipulation of cells and molecules, Biosensors and Bioelectronics 85 (2016) 714-725.
Weiwei Cui, Bulk Acoustic Wave Resonator Integrated Microfluidics for Rapid and High Efficiency Fluids Mixing and Bioparticle Trapping, 2016 IEEE International Ultrasonics Symposium (IUS), IEEE, Sep. 18, 2016, XP032988257, DOI:10.1109/ULTSYM.2016. 7728375.
Wang, Zhuochen et al., Recent advances in particle and droplet manipulation for lab-on-a-chip devices based on surface acoustic waves, Lab Chip, 2011, 11, 1280.
Dario Carugo et al., Contrast agent-free sonoporation: The use of an ultrasonic standing wave microfluidic system for the delivery of pharmaceutical agents, Biomicrofluidics 5, 044108 (2011).

Y-H Lee et al., Enhanced retroviral gene delivery in ultrasonic standing wave fields, Gene Therapy (2005) 12, 625-633.
Response to extended European search report dated Aug. 17, 2020 in European Patent Application No. EP18750728.0 (60 pages).
The extended European search report dated Jan. 21, 2020 in European Patent Application No. 18750728.0 (10 pages).
Communication pursuant to Rules 70(2) and 70a(2) EPC dated Feb. 7, 2020 in European Patent Application No. 18750728.0 (1page).
Meacham, J. Mark et al., Physical Methods for Intracellular Delivery: Practical Aspects from Laboratory Use to Industrial-Scale Processing, J Lab Autom. Feb. 2014; 19(1): 1-18. Doi:10.1177/ 2211068213494388.
Meacham, J. Mark et al., Enhanced intracellular delivery via coordinated acoustically driven shear mechanoporation and electrophoretic insertion, Scientific Reports, (2018) 8:3727,DOI:10. 1038/s41598-018-22042-0.
Zarnitsyn, Vladimir G. et al., Electrosonic ejector microarray for drug and gene delivery, Biomed Microdevices (2008) 10:299-309; DOI 10.1007/s10544-007-91374.
PCT International Search Report for PCT/US2018/017965, Applicant: The Regents of the University of California, Form PCT/ISA/ 210 and 220, dated Apr. 13, 2018 (4 pages).
PCT Written Opinion of the International Search Authority for PCT/US2018/017965, Applicant: The Regents of the University of California, Form PCT/ISA/237, dated Apr. 13, 2018 (10 pages).
Gill, HS, Coated microneedles and microdermabrasion for transdermal delivery, a dissertation, Georgia Institute of Technology, Aug. 2007. [Retrieved from the internet on Mar. 19, 2018]. <URL: https:l/smartech.gatech.edu/handle/1853/24711>; pp. 54, 73, 85, 88, 96.
Han, X et al., CRISPR-Cas9 delivery to hard-to-transfect cells via membrane deformation. Science advances, vol. 1, No. 7. Aug. 1, 2015; abstract; pp. 1-2, 4, 6-7.
JO, MC, An acoustic-based microfluidic platform for active separation and mixing, University of South Florida, a dissertation, 2013, (Retrieved from the internet on Mar. 15, 2018] <URL: http:// scholarcommons.usf.edu/cgi/viewcontent.cgi?article=5894&context= etd>; pp. 19, 28, 30,37-39,42-44,60,63,74.
Chiappini, C. et al., Biodegradable silicon nanoneedles delivering nucleic acids intracellularly induce localized in vivo neovascularization, Nat Mater. May 2015 ; 14(5): 532-539. doi:10.1038/nmat4249.
Ding, X. et al., Surface acoustic wave microfluidics, Lab Chip. Sep. 21, 2013; 13(18): 3626-3649. doi:10.1039/c3lc50361e.
Fan, Z. et al., Mechanisms of microbubble-facilitated sonoporation for drug and gene delivery, Ther Deliv. Apr. 2014 ; 5(4): 467-486. doi:10.4155/tde.14.10.
Jordan, E.T., et al., Optimizing Electroporation Conditions in Primary and Other Difficult-to-Transfect Cells, Journal of Biomolecular Techniques 1 RF 9:328-334 (2008).
Luo, J.K. et al., Acoustic Wave Based Microfluidics and Lab-on-a-Chip, Acoustic Wave Based Microfluidics and Lab-on-a-Chip, http://dx.doi.org/10.5772/56387 (2013).
Shalek, A. K. et al., Vertical silicon nanowires as a universal platform for delivering biomolecules into living cells, 1870-1875, PNAS, Feb. 2, 2010, vol. 107, No. 5.
Shareia, A. et al., A vector-free microfluidic platform for intracellular delivery, 2082-2087, PNAS, Feb. 5, 2013, vol. 110, No. 6.
Shi, J. et al., Three-dimensional continuous particle focusing in a microfluidic channel via standing surface acoustic waves (SSAW)†, Lab Chip. Author manuscript; available in PMC Apr. 23, 2014.
Tomizawa, M. et al., Sonoporation: Gene transfer using ultrasound, World J Methodol Dec. 26, 2013; 3(4): 39-44.
Yin, H. et al., Therapeutic genome editing by combined viral and non-viral delivery of CRISPR system components in vivo, Nat Biotechnol. Mar. 2016 ; 34(3): 328-333. doi:10.1038/nbt.3471.
Liang, H.D. et al., Sonoporation, drug delivery, and gene therapy, Proc. IMechE vol. 224 Part H: J. Engineering in Medicine, JEIM565, https://www.researchgate.net/publication/42637765 (2010).
Golshadi, M. et al., High-Effi ciency Gene Transfection of Cells through Carbon Nanotube Arrays, small 2016, 12, No. 22, 3014-3020.

(56) References Cited

OTHER PUBLICATIONS

Gillmor, S.D. et al., Dimpled Vesicles: The Interplay between Energetics and Transient Pores, J. Phys. Chem. B 2008, 112, 13629-13634.

* cited by examiner

DEVICE AND METHOD FOR INTRACELLULAR DELIVERY OF BIOMOLECULAR CARGO VIA ACOUSTIC WAVE EXPOSURE

RELATED APPLICATION

This Application is a U.S. National Stage filing under 35 U.S.C. § 371 of International Application No. PCT/US2018/017965, filed Feb. 13, 2018, which claims priority to U.S. Provisional Patent Application No. 62/458,289 filed on Feb. 13, 2017, which are hereby incorporated by reference. Priority is claimed pursuant to 35 U.S.C. §§ 119, 371 and any other applicable statute.

This invention was made with government support under Grant Numbers HL119893 and TR001881, awarded by the National Institutes of Health. The government has certain rights in the invention.

TECHNICAL FIELD

The technical field generally relates to microfluidic devices and in particular microfluidic devices that are used for intracellular cargo delivery to cells using exposure to bulk acoustic waves transduced from surface acoustic waves (SAWs) generated by a rapidly oscillating piezoelectric substrate or piezoelectric material.

BACKGROUND

Gene therapy and gene modification technologies are increasingly being studied, investigated, and used for clinical applications. In order to modify or alter genes, the gene-editing biomolecules or other constructs need to be delivered into cells. Currently, a standard technique for gene modification uses lentiviral-based vector systems. Lentiviruses can deliver a significant amount of genetic information into DNA of the host cell so they are one of the most effective methods of a gene delivery vector. Electroporation, in which an electrical field is applied to cells in order to increase the permeability of the cell membrane, is another technique that has been used to transfect cells for gene therapy based on targeted endonucleases. Chemical transfection methods may also be used for gene-editing applications based on targeted endonucleases. Conventional electroporation, however, suffers from toxicity problems as well as technical limitations in using this method in scaled-up clinical applications.

Other approaches for intracellular delivery of biomolecules involving nanoparticles or nanostructures (e.g., nanostraws, carbon nanotubes, or needles) have been demonstrated but have not been commercialized or scaled up for clinicial use. Intracellular delivery of biomolecules by physical deformation of cell membranes within microfluidic channels has also been demonstrated. For example, Sharei et al. have demonstrated that transient holes are formed in cell membranes that pass through a microfluidic constriction that applies compression and shear forces on cells. See Sharei et al., A Vector-Free Microfluidic Platform for Intracellular Delivery, *Proceedings of the National Academy of Sciences* 110, pp. 2082-87 (2013). Biomolecules, such as genes, have also been delivered intracellular via sonoporation, where pores across the cell membrane are created by ultrasonically induced cavitation microbubbles. For example, Fan et al. describe the use of ultrasound to induce rapid expansion/contraction and/or collapse of microbubbles which can be used to temporarily increase the cell membrane permeability. See Fan et al., Mechanisms of Microbubble-Facilitated Sonoporation for Drug and Gene Delivery, *Therapeutic Delivery* 5, pp. 467-86 (2014).

Unfortunately, these techniques are limited by low efficiency of gene transfer and sonoporation can lead to cell death due to irreversible damage to the cell membrane. In addition, target cells are often required to be stationary and fixed in place during sonoporation, which limits achievable throughputs. While intracellular delivery through cell membrane deformation is beginning to emerge, current embodiments of this technology also suffer from issues with fouling, which affects long-term reliability of these devices and efforts for translation towards clinically relevant applications. There is a need in stem cell biology applications as well as next-generation gene and immunotherapies for high-throughput and efficient methods of delivering biomolecules to eukaryotic cells, bacteria, or enveloped viruses.

SUMMARY

In one embodiment of the invention, a microfluidic-based device is disclosed for high-throughput intracellular cargo (e.g., biomolecules) delivery to eukaryotic cells, prokaryotic cells (i.e., bacteria), or enveloped viruses. Cargo integration occurs due to transient membrane permeabilization by exposure to bulk acoustic waves (BAWs) transduced from surface acoustic waves (SAWs) generated by a rapidly oscillating piezoelectric substrate. In this approach, temporary pores are established across the cellular membrane as cells are partially deformed and squeezed or encouter shear stresses as the cells travel through the vibrational modes created within the microchannel of the device. The frequency and amplitude of the piezoelectric oscillations are tuned to one or more resonant frequencies of the cell or parts thereof enabling the near-threshold or threshold vibrational amplitude(s) necessary for cargo integration. Specifically, the intensity(/ies) of the oscillations at the resonance frequency(/ies) are tuned to minimize the energy necessary for delivery and thus damage to the cells.

In one particular embodiment, a microfluidic device for the intracellular delivery of biomolecular cargo includes a piezoelectric substrate and a microfluidic substrate disposed on the piezoelectric substrate and having one or more microfluidics channels disposed therein. The signal generator is coupled to the piezoelectric substrate. In one embodiment, actuation of the piezoelectric substrate by the signal generator creates BAWs that push or move the cells against an inner surface of the one or more microfluidic channels. The inner surface of the one or more microfluidic channels may be functionalized with silane (e.g., a solution of 5% (v/v) ethanolic solution of (3-aminopropyl)triethoxysilane (APTES)) to render the inner surface positively charged. Plasmids containing nucleic acids are flowed through the microfluidic device where the plasmids adhere or become tethered to the positively charged inner surface. Cells are then flowed through the one or more microfluidic channels and the piezoelectric substrate is actuated to permeabilize and move the cells toward the inner surface containing the plasmids which effectuates transfection of the cells.

In another embodiment, a method of using the microfluidic device includes flowing a solution containing cells or enveloped viruses and the biomolecular cargo through the one or more microfluidic channels and powering the piezoelectric substrate with the signal generator while the solution containing cells or enveloped viruses and the biomolecular cargo passes through the one or more microfluidic channels adjacent to the piezoelectric substrate.

In another embodiment, a method of using the microfluidic device includes flowing a solution containing the biomolecular cargo through the one or more microfluidic channels, wherein the biomolecular cargo adheres to one or more interior surfaces of the one or more microfluidic channels; flowing a solution containing cells or enveloped viruses through the one or more microfluidic channels; and powering the piezoelectric substrate with the signal generator while the solution containing cells passes through the one or more microfluidic channels adjacent to the piezoelectric substrate.

In another embodiment, a microfluidic device for the intracellular delivery of biomolecular cargo includes a piezoelectric substrate having a microfluidic channel disposed on a surface thereof and a first pair of interdigitated electrodes (IDTs) disposed on opposing sides of the microfluidic channel at a first location along the microfluidic channel. A signal generator is provided that is configured to apply an AC voltage to the first pair of IDTs. In another embodiment, a second pair of interdigitated electrodes (IDTs) is disposed on opposing sides of the microfluidic channel at a second location along the microfluidic channel, the second location being located downstream of the first location. Optionally, an acoustic damper may be interposed between the first pair of interdigitated electrodes (IDTs) and the second pair of interdigitated electrodes (IDTs).

In yet another embodiment, a microfluidic device for the intracellular delivery of biomolecular cargo includes a piezoelectric substrate having a plurality of microfluidic channels disposed on a surface thereof. A first plurality of respective pairs of interdigitated electrodes (IDTs) are disposed on opposing sides each of the plurality of microfluidic channels at a first location along the plurality of microfluidic channels. A signal generator is provided and configured to apply an AC voltage to the first plurality of respective pairs of interdigitated electrodes (IDTs).

In still another embodiment, a second plurality of respective pairs of interdigitated electrodes (IDTs) are disposed on opposing sides of each of the plurality of microfluidic channels at a second location along the plurality of microfluidic channels, the second location being located downstream of the first location. Optionally, an acoustic damper may be interposed between the first plurality of respective pairs of interdigitated electrodes (IDTs) and the second plurality of respective pairs of interdigitated electrodes (IDTs).

In another embodiment, the inner surface of the microfluidic channels may include nanostructured features that extend or otherwise project inwardly from the inner surface of the microfluidic channel(s). The nanostructured features may aid in the delivery of biomolecular cargo into the interior of cells, bacteria, or enveloped viruses.

BRIEF DESCRIPTION OF THE DRAWINGS

FIG. 9 illustrates off-chip circuitry used to power interdigitated electrodes (IDTs).

DETAILED DESCRIPTION OF THE ILLUSTRATED EMBODIMENTS

Figure 1:
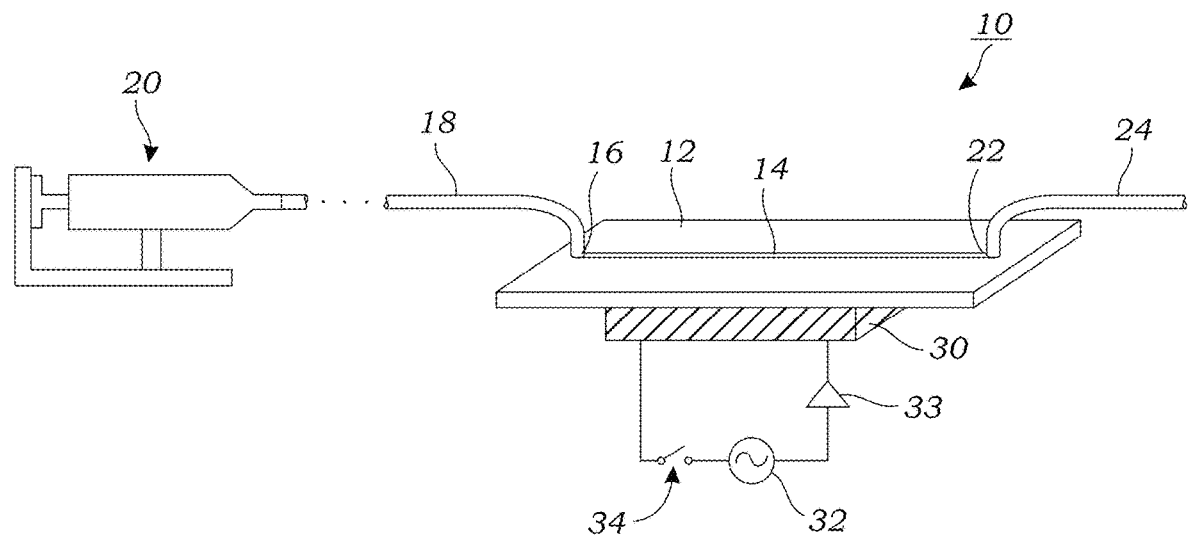
FIG. 1 illustrates one embodiment of a system for the intracellular delivery of biomolecular cargo to living cells via vibrational cell deformability. A single microfluidic channel is illustrated. It should be appreciated that while a cell is illustrated, the system may also be used with bacteria or enveloped viruses.

FIG. 1 illustrates one embodiment of a system 10 for the intracellular delivery of biomolecular cargo 44 (illustrated in FIGS. 4B, 5, 9) to living eukaryotic or prokaryotic cells 100 (illustrated in FIGS. 3C, 4A, 4B, 5, 8, 9) via vibrational cell deformability. While the system 10 is described herein is illustrated as being used with eukaryotic cells 100 (e.g., mammalian cells 100) it should be appreciated that the system 10 may also be used for the intracellular delivery of biomolecular cargo 40 to living prokaryotic cells 100 (i.e., bacteria) as well as enveloped viruses. An enveloped virus is virus that has an outer wrapping or envelop that comes from an infected cell 100 or host. While the embodiments described herein are described in the context of cells 100 it should be appreciated that enveloped viruses may be interchangeable with the term "cells" when used herein. The system 10 includes a microfluidic device 12 that has one or more microfluidic channels 14 formed therein. The microfluidic device 12 may be formed from one or more layers or substrates that collectively define the microfluidic device 12 and define the microfluidic channel(s) 14. Alternatively, the microfluidic device 12 may be made from a single substrate. For example, the microfluidic device 12 may be formed from any number materials including, for example, silicon, quartz, lead zirconate titanate, lithium niobate ($LiNbO_3$), fused silica, glass, ceramics, polymers, and metals. In some embodiments, a combination of materials may be used. For example, a piezoelectric substrate or material that forms the acoustic transmitting element may be bonded or adhered to another substrate (e.g., glass). Alternatively, the microfluidic channel 14 may be formed directly in or part of the piezoelectric substrate or material (e.g., quartz, lead zirconate titanate, lithium niobate ($LiNbO_3$), or the like).

As one example, the microfluidic channel(s) 14 may be formed in or defined by polydimethylsiloxane (PDMS) which is then bonded to another substrate such as quartz, lead zirconate titanate, lithium niobate ($LiNbO_3$). Methods and techniques for forming microfluidic devices 12 using PDMS are well known. Typically these are formed using soft lithography methods. In soft lithography a negative photoresist is typically spun on a substrate such as silicon, soft-baked and then exposed under a mask to radiation to define the channels that will be formed in the microfluidic device 12. The exposed photoresist is developed and cleaned to define a master mold. PDMS and a curing agent are then poured on the master mold and allowed to cure. The PDMS material that contains the channels 14 is then removed from the master mold and then bonded to a substrate (e.g., quartz, lead zirconate titanate, lithium niobate ($LiNbO_3$), or the like) such as using oxygen plasma. Alternatively, three-dimensional (3D) printing technologies can be used which are known to be used to develop rapid prototypes and the design of microfluidic systems with complex, 3D channel networks. These alternative manufacturing techniques may be used to create microfluidic channels 14 made from materials other than PDMS.

As seen in FIG. 1, the microfluidic device 12 includes an inlet 16 that is coupled to the microfluidic channel 14. A segment of tubing 18 or the like can be inserted into the inlet 16 and is used to deliver fluids to the microfluidic device 12 as explained herein. In FIG. 1, the tubing 18 is connected to a pump 20 that is used to pump fluid containing biomolecular cargo 44 and cells 100 into the microfluidic device 12. The fluid that contains the cells 100 and biomolecular cargo 44 may include a buffer solution or the like is well-tolerated by the cells 100. In one example, the pump 20 may include a syringe pump (e.g., Fusion 4000, Chemyx, Inc., Stafford, Tex.) although it should be appreciated that other types of pumps that are used in connection with microfluidic devices 12 may also be used. While FIG. 1 illustrates a single pump 20, it should be appreciated that the different solutions (e.g., fluid containing cells 100, fluid containing biomolecular cargo 44, fluid containing a vector 45) could be pumped using separate pumps 20 that are then combined or mixed prior to entering the microfluidic channel 14.

The microfluidic device 12 further includes an outlet 22 that is coupled to the microfluidic channel 14. A segment of tubing 24 or the like can be inserted into the outlet 22 and carries fluid leaving the microfluidic device 12. While an outlet 22 is illustrated it should be appreciated that the microfluidic device 12 may not include an outlet as downstream processed fluid may pass to another area or region of the microfluidic device 12 (e.g., chambers, other channels, etc.) or may pass to another microfluidic device 12.

Still referring to FIG. 1, system 10 includes a piezoelectric substrate 30 that is in direct or indirect contact with or defines one or more surfaces of the microfluidic device 12. The piezoelectric substrate 30 may include a piezoelectric transducer or plate in some embodiments. In one embodiment, the piezoelectric substrate 30 is a commercially available PZT transducer or plate such as, for example, lead zirconate titanate (PZT) transducer plates available from STEMiNC, Doral, Fla. (part no. SMPL26W16T07111). The piezoelectric substrate 30 may be bonded to or otherwise adhered to the surface of the microfluidic device 12 or formed integrally as part of the microfluidic device 12. For example, the piezoelectric substrate 30 may be secured to the microfluidic device 12 using an adhesive such as an epoxy. The piezoelectric substrate 30 has a contact surface with the microfluidic device 12 that extends across the width of the microfluidic channel 14. The piezoelectric substrate 30 is connected to a signal generator 32 which is used to apply an alternating current (AC) to the piezoelectric substrate 30. In one embodiment, the signal from the signal generator 32 may be amplified using amplifier 33 (e.g., 25A250B 25 Watt CW, 10 kHz-250 MHz power amplifier, AR Products, Souderton, Pa.). In some embodiments, the signal generator 32 may be sufficient to provide the amplified voltage to the piezoelectric substrate 30, in which case the separate amplifier 33 may be omitted.

The signal generator 32 may be turned on/off using switch 34, which may be integrated into the signal generator 32 or other off-chip circuitry. In one preferred embodiment, the frequency of the AC current that is applied to the piezoelectric substrate 30 may be adjustable or tunable. In this regard, different vibrational frequencies may be applied to the microfluidic device 12 using the piezoelectric substrate 30. Different applied AC frequencies generate different resonant frequencies in the piezoelectric substrate 30 which can be used to generate bulk acoustic waves (BAWs) that are transduced from surface acoustic waves (SAWs) generated by the rapidly oscillating piezoelectric substrate 30. As explained in more detail herein, the BAWs create a transient permeabilization of cell membranes of cells 100 (seen in FIGS. 3C, 4A, 4B, 5, 8, and 9) that are passing through the microfluidic channel 14 that enables biomolecular cargo 44 to pass from the external cellular environment to the intracellular space.

In this approach, temporary pores are established across the cellular membrane as cells 100 are partially deformed and squeezed or subject to shear forces as the cells 100 travel through the vibrational modes created within the microfluidic channel 14 of the microfluidic device 12. The frequency and amplitude of the piezoelectric oscillations created by the piezoelectric substrate 30 are tunable by the signal generator 32 to one or more resonant frequencies of the cell 100 or parts thereof enabling the near-threshold or threshold vibrational amplitude(s) necessary for biomolecualr cargo 33 integration. Specifically, the intensity(/ies) of the oscillations at the resonance frequency(/ies) are tuned to minimize the energy necessary for delivery and thus damage to the cells 100. The frequency requirements for cell membrane resonance (and pore formation) are typically in the range of the kHz-MHz range. For the embodiment of FIG. 1, a frequency range within about 1 MHz and about 10 MHz was used, although in other constructions, different frequencies may still be employed that produce resonant harmonics in the piezoelectric substrate 30. The amplitude of the applied AC signal may also vary. Typically, the maximum voltage that is applied is about 40 V (peak-to-peak or $40V_{p-p}$). Additional voltages above this limit may be used but may require one or more active cooling elements to cool the microfluidic device 12 because of heat generation issues. Voltages below this may also be used although lower transfection efficiency may result.

The different resonant frequencies of the microfluidic device 12 constructed with the piezoelectric substrate 30 may be first detected using a vector network analyzer (e.g., VNA-120, Array Solutions, Sunnyvale, Tex.) that is used to determine the different harmonic resonant frequencies of the piezoelectric substrate 30. During operation of the system 10 as explained herein, the piezoelectric substrate 30 is driven at one of these harmonic resonant frequencies. By using one of the resonant frequencies of the piezoelectric substrate 30, this ensures that high strength BAMs are imparted on the cells 100 in the microfluidic channels 14. Because there may be a plurality of harmonic resonant frequencies, these different frequencies may be experimentally tested to determine which frequencies should be used for the particular application of interest. For example, in one embodiment, polystyrene beads that approximate the size of cells 100 may be first run through the microfluidic device(s) 12 described herein to determine the physical location of the beads (and thus cells 100 by proxy) in response to a particular applied frequency. For example, as described herein, in certain embodiments it is desirous to push or move the cells 100 toward a surface of the microfluidic channel 14 (e.g., apply shear to the cells 100). The polystyrene beads may be used to find out what frequency is best to move the cells 100 toward the surface to promote surface interactions with either the surface of the microfluidic channel 14 or biomolecular cargo 44 that is tethered or otherwise adhered to the surface of the microfluidic channel 14.

Figure 2:
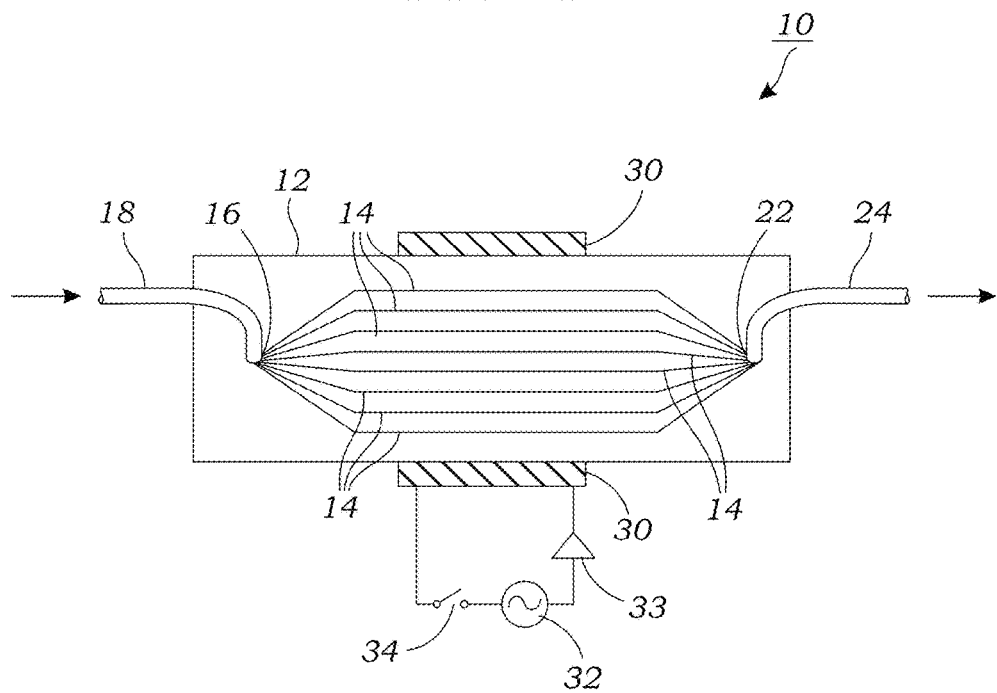
FIG. 2 illustrates another embodiment of a system for the intracellular delivery of biomolecular cargo to living cells via vibrational cell deformability. In this embodiment, a plurality of microfluidic channels are included in the device to increase cell throughput.

FIG. 2 illustrates another embodiment of the microfluidic device 12. In this embodiment, similar reference numbers are given to similar elements to those of FIG. 1. In this embodiment, the microfluidic device 12 includes a plurality of microfluidic channels 14. As seen in FIG. 2, the plurality of microfluidic channels 14 are arranged in a generally parallel array whereby a common inlet 16 feeds the various microfluidic channels 14. This embodiment permits the delivery of biomolecular cargo 44 to large numbers of cells 100 due to the use of parallel processing along the plurality of microfluidic channels 14. This further enables the use of less concentrated flows of cells 100 within individual microfluidic channels 14 which may tend to become fouled and clogged. The microfluidic device 12 of FIG. 2 operates in the same manner with the inlet 16 being coupled to a pump 20 (not illustrated) which is used to pump the fluid containing the cells 100, biomolecular cargo 44, vectors 40, etc. through the microfluidic channels 14.

It should be appreciated that in some embodiments described herein, the microfluidic channel(s) 14 and the application of BAWS therein can operate on a single cell 100 or enveloped virus at a time. Alternatively, the microfluidic channel(s) 14 and the application of BAWS therein can operate on a multiplicity of cells 100 or enveloped viruses at a time.

Figure 3A:
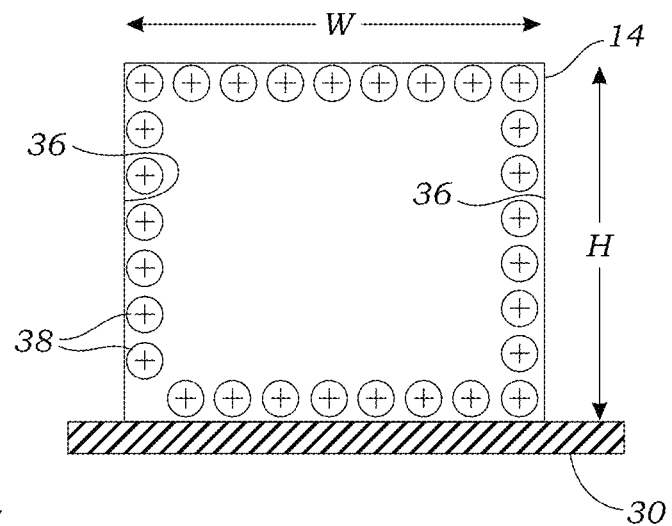
FIG. 3A illustrates a cross-sectional view of the microfluidic channel of the embodiment of FIG. 1. The inner surface of the microfluidic channel has been functionalized with a solution of 5% (v/v) ethanolic solution of (3-aminopropyl)triethoxysilane (APTES) and dried.

FIG. 3A illustrates a cross-sectional view of a single microfluidic channel 14 according to one embodiment. The microfluidic channel 14 has a rectangular cross-section having a height (H) and width (W). Generally, the height (H) may be within the range of about 20 μm to about 200 μm. The width (W) may be within the range of about 20 μm to about 200 μm. While a rectangular cross-section is illustrated it should be appreciated that other cross-sectional shapes for the microfluidic channel 14 may be used in connection with the methods described herein. FIG. 3A illustrates a microfluidic channel 14 that has an inner surface 36 that has been functionalized with positvely charged molecules 38. As one example, the positively charged molecules 38 include a silane-funtionalized surface having a positively charged amino group that is exposed to the inner volume of the microfluidic channel 14. The inner surface 36 may be functionalized by running a 5% (v/v) ethanolic solution of (3-aminopropyl)triethoxysilane (APTES) and dried. In this example, the inner surface 36 is rendered positively charged to electrostatically attract and adhere vectors 40 such as plasmids as described herein. Of course, other chemically functionalized approaches may be used for the inner surface 36. For example, a self-assembled monolayer may be formed on the inner surface 36.

Figure 3B:
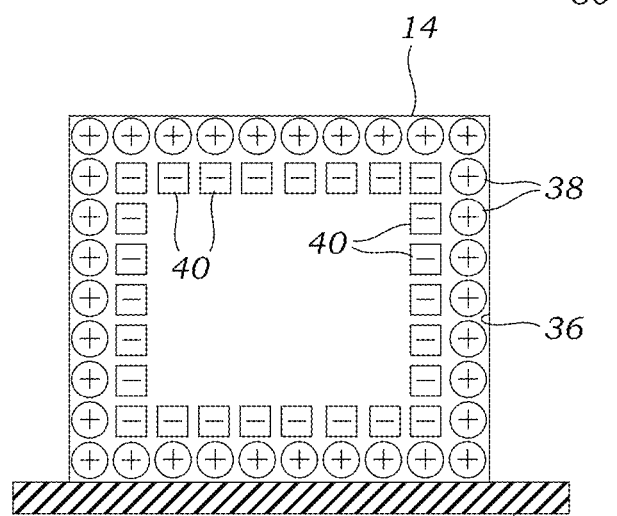
FIG. 3B illustrates the same cross-sectional view of the microfluidic channel of FIG. 3A after a negatively charged vector (e.g., plasmid) has been flowed through the microfluidic channel.

FIG. 3B illustrates another cross-sectional view of the microfluidic channel 14 after negatively charged vectors 40 (vectors 40 are one example of biomolecular cargo 45) have been flowed through the microfluidic channel 14. As seen in FIG. 3B, the negatively charged vectors 40 adhere to a region near the inner surface 36 of the microfluidic channel 14. In one aspect, the negatively charged vectors 40 are tethered to the inner surface 36 by electrostatic forces between the negatively charged vectors 40 and the postively charged molecules 38 that are functionalized to the inner surface 36. For example, plasmids contain deoxyribonucleic acid (DNA) that is negatively charged. Plasmids are thus one type of negatively charged vector 40 that contain the biomolecular cargo 44 (e.g., genes or gene fragments that can be transported into the the interior of the cells 100. While electrostatic bonds secure the negatively charged vectors 40 to the inner surface 36 in this embodiment, in other embodidments, vectors 40 (which may or may not be electrically charged) or other biomolecular cargo 44 may be covalently bound to the inner surface 36.

Figure 3C:
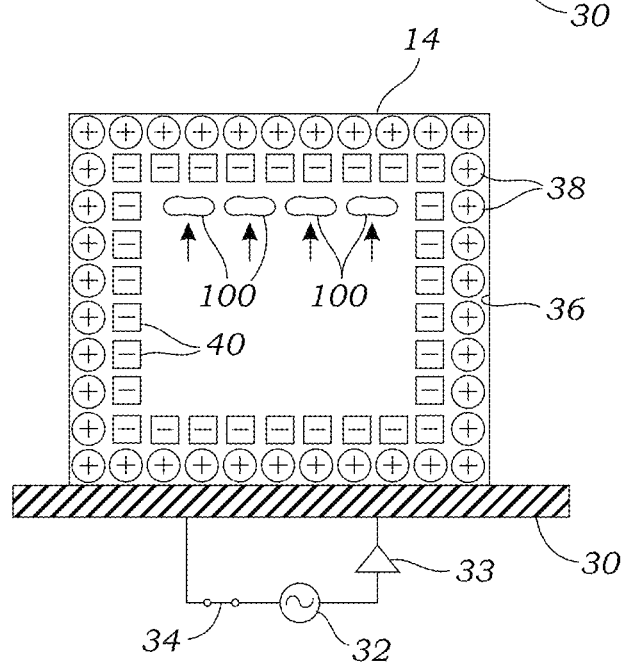
FIG. 3C illustrates the same cross-sectional view of the microfluidic channel of FIG. 3A after cells are flowed through the microfluidic channel and the piezoelectric substrate is activated via off-chip circuitry.

FIG. 3C illustrates another cross-sectional view of the microfluidic channel 14 after cells 100 have been flowed through the microfluidic channel 14 of FIG. 3B and the piezoelectric substrate 30 has been activated via the signal generator 32. As seen in FIG. 3C, the cells 100 are pushed by the bulk acoustic waves (BAWs) generated within the microfluidic channel 14 toward the inner surface 36 of the microfluidic channel 14. The cells 100 are thus in contact with or close proximity to the biomolecular cargo 45, namely, the negatively charged vectors 40 (e.g., plasmids). Likewise, the application of the BAWs induces the formation of temporary pores in the cells 100 as the cells 100 are partially deformed and squeezed and subject to shear forces as the cells 100 travel through the vibrational modes created within the microfluidic channel 14 of the microfluidic device 12.

Figure 4A:
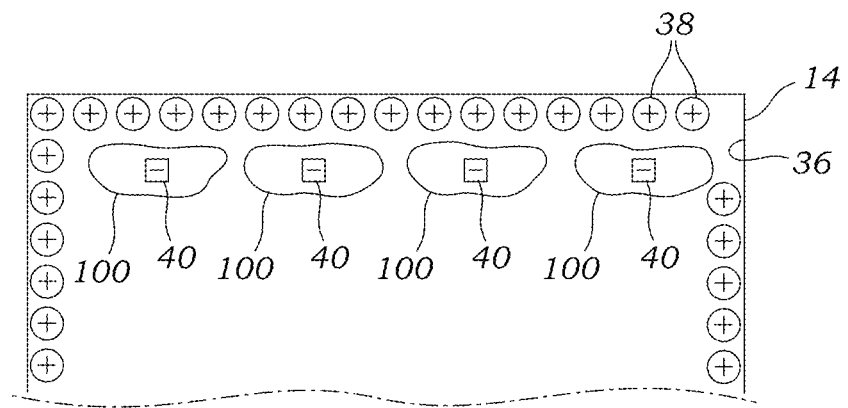
FIG. 4A illustrates a cross-sectional view of a microfluidic channel showing transfection of cells with biomolecular cargo (i.e., plasmid vector in this particular instance).

FIG. 4A illustrates a partial cross-sectional view of the microfluidic channel 14 illustrating the negatively charged vector 40 that has been delivered inside the cells 100 in response to the applied vibrational energy the microfluidic device 12. While a negatively charged vector 40 is illustrated as having passed into the interior of the cells 100 in FIG. 4A it should be understood that a variety of different types of biomolecular cargo 44 may be incorporated into cells 100 using the devices and methods described herein. The biomolecular cargo 44 may include, for example, a molecule, multiple molecules, or higher order biological constructs. For example, molecules may include antigens, antibodies, proteins, protein fragments, enzymes, enzyme fragments, nucleic acids, interfering RNA, transcription factors, nuclease gene-editing molecules or transcription activator-like effector nucleases, and the like. As one example, biomolecular cargo 44 may include, by way of illustration and not limitation, plasmids and/or targeted nucleases for gene-editing, e.g., CRISPR constructs such as guide RNA, Cas9 protein, Cas9 mRNA or ribonucleoprotein, associated guide RNA sequences, homologous donor template nucleic acids, and the like. One particular example of gene-editing molecules includes the CRISPR-Cas9 nuclease system that includes single-guide RNA (sgRNA) and the enzyme Cas9. The sgRNA directs the Cas9 nuclease to introduce sequence-specific targeted insertions, deletions, and genetic edits at specific genetic targets. Additional details regarding the CRISPR-Cas 9 may be found in Doudna et al., Genome editing. The new frontier of genome engineering with CRISPR-Cas9, Science, Vol. 346, Issue 6213 (2014), which is incorporated herein by reference.

In some embodiments, the biomolecular cargo 44 is delivered intracellularly into the cells 100 with the aid of a vector 40 in response to applied vibrational energy. The vector 40 may be negatively charged such as the plasmid described herein but in other embodiments, it may be neutral or even positively charged. In other embodiments, the biomolecular cargo 44 is delivered intracellularly into the cells 100 without the aid of a vector 46 in response to applied vibrational energy. That is to say, the biomolecular cargo 44 traverses the membrane of the cell 100 directly without the aid of a carrier or the like.

In some embodiments, the biomolecular cargo 44 may be delivered or flowed through the microfluidic channel 14 at the same time that the cells 100 are flowed through the microfluidic channel 14. For example, the cells 100 and biomolecular cargo 44 may be co-flowed through the microfluidic device 12. A single solution containing both the biomolecular cargo 44 and the cells 100 may be pumped through the device. Alternatively, separate solutions containing the cells 100 and the biomolecular cargo 44 may be mixed and simultaneously pumped through the microfluidic device 12. In yet another embodiment, the biomolecular cargo 44 and cells 100 may be delivered sequentially. For example, as explained with regard to the embodiments of FIGS. 3A-3C, a solution containing the negatively charged vector 40 may be flowed through the microfluidic channel 14 followed by a solution containing the cells 100. The negatively charged vector 40 (e.g., plasmid) becomes tethered to the inner surface 36 of the microfluidic channel 14 which can then interact with the subsequently delivered cells 100 and transfect the cells 100 to insert the genomic information into the transfected cell 100.

Figure 4B:
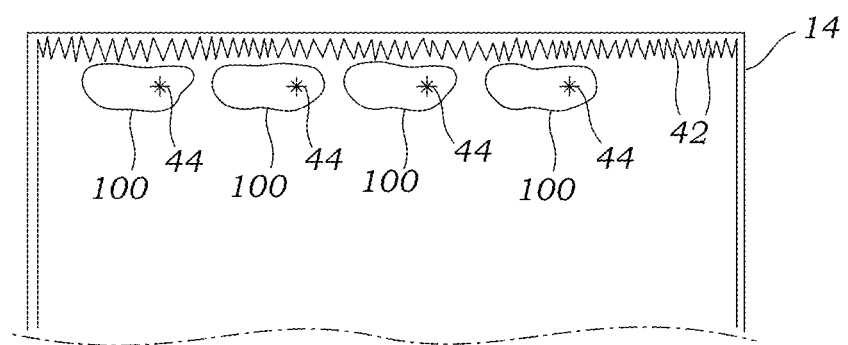
FIG. 4B illustrates a cross-sectional view of another microfluidic channel showing transfection of cells with biomolecular cargo (i.e., plasmid vector in this particular instance). This embodiment utilizes nanostructured features that are formed on an inner surface of the microfluidic channel.

FIG. 4B illustrates a partial cross-sectional view of the microfluidic channel 14 according to one embodiment. In this embodiment, all or a portion of the microfluidic channel 14 contains a plurality of nanostructured features 42 that extend or otherwise project inwardly from the inner surface 36 of the microfluidic channel 14. Nanostructured features 42 are nanometer-sized or micron-sized protrusions or protuberances that extend into the flow channel. Nanostructured features 42 may extend for a distance of tens of nanometers up to several microns. Nanostructured features 42 may include any number of shapes of protuberances that extend into the flow path. These may include pillars, posts, wires, tubes, cones, pyramids, needles, and the like. The nanostructured features 42 may be formed using lithographic techniques including electron-beam and nanosphere lithography. In nanosphere lithography, periodic arrays of self-assembled close-packed nanospheres are used as masks to pattern underlying substrate materials. Details regarding nanosphere lithography may be found in Xu et al., Multiple-Patterning Nanosphere Lithography for Fabricating Periodic Three-Dimensional Hierarchical Nanostructures, ACS Nano, 11, pp. 10384-391 (2017), which is incorporated herein by reference.

Reactive ion etching or the like may also be used to form the nanostructured features 42 with appropriate masking. The nanostructured features 42 may be formed on all exposed surfaces of the microfluidic channel 14. Alternatively, less than all of the surfaces in the microfluidic channel 14 may contain nanostructured features 42. For example, only a single surface or two of four surfaces may contain nanostructured features 42 (e.g., top and bottom). The nanostructured features 42 preferably are formed in that region of the microfluidic channel 14 that overlies the piezoelectric substrate 30. For example, the nanostructured features 42 may be formed on the substrate made from a polymer, silicon or glass that is then used to form the top and/or bottom of the microfluidic device 12. The nanostructured features 14 may be used to aid in permeabilizing the cells 100 that pass through the microfluidic channel 14. For example, the tips or ends of the nanostructured features 42 may be sharpened to aid in physically disrupting the membranes of the cells 100 (or the envelope of viruses). The nanostructured features 42 may also be functionalized to attract or repel cells 100 or cells 100 of certain types. As seen in FIG. 4B, biomolecular cargo 44 are illustrated inside the cells 100 having been assisted by the presence of the nanostructured features 42.

Figure 5:
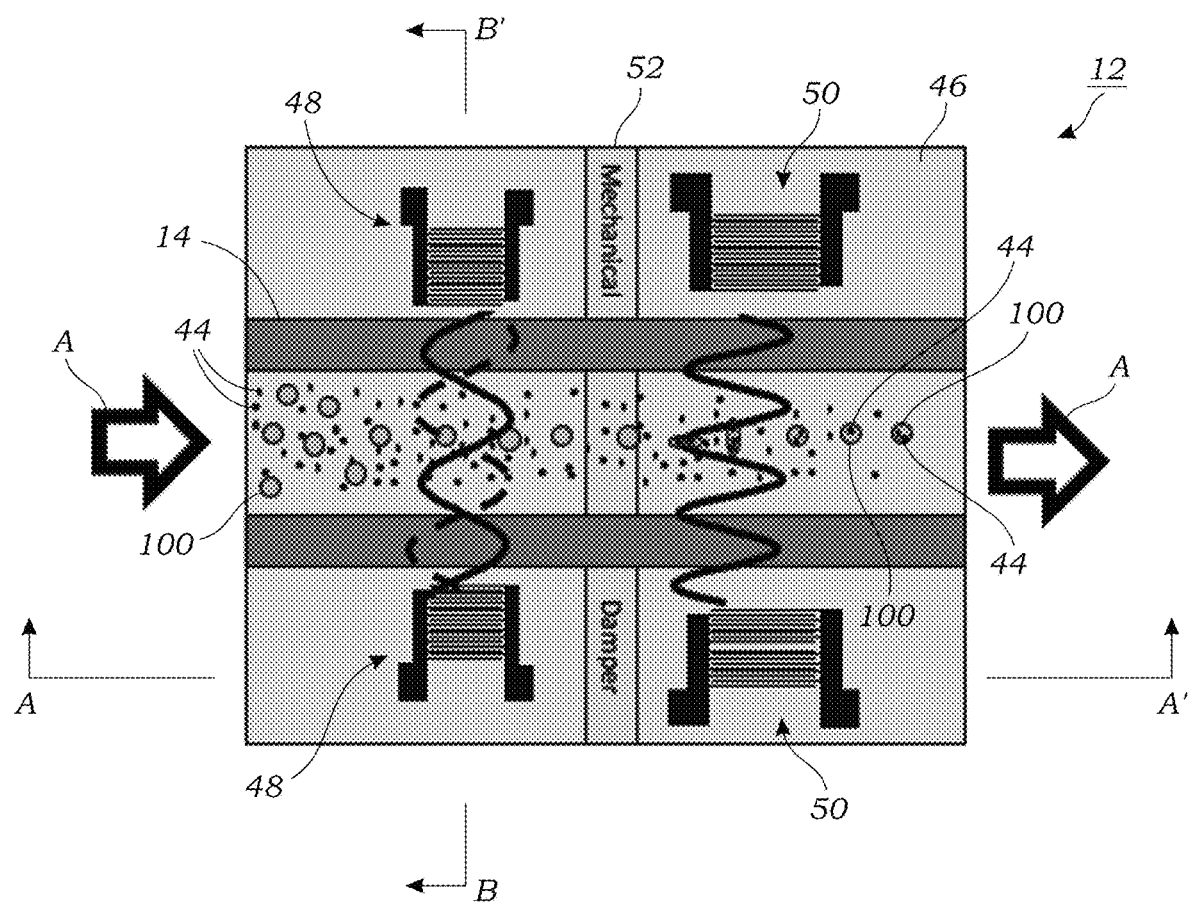
FIG. 5 illustrates a plan view of another embodiment of a system for the intracellular delivery of biomolecular cargo to living cells.

FIG. 5 illustrates a microfluidic device 12 according to another embodiment for the intracellular delivery of biomolecular cargo 44 to living cells 100 via vibrational cell deformability. As explained herein, the microfluidic device 12 may include a microfluidic channel 14 made from, for example, polydimethylsiloxane (PDMS) that is bonded to or sealed with respect to a piezoelectric substrate 46. The microfluidic device 12 includes, in a preferred embodiment, one or more microfluidic channels 14 having diameters (or widths) on within the range of about 20 µm-200 µm to allow for the transport of the desired cells 100. FIG. 5 illustrates a single microfluidic channel 14 but it should be appreciated that in other embodiments a plurality of microfluidic channels 14 may be used to enable the high-throughput of larger numbers of cells 100 through the microfluidic device 12. In this embodiment, the microfluidic channel(s) 14 is/are secured to or formed on a piezoelectric substrate 46 such as lead zirconate titanate, lithium niobate (LiNbO$_3$), or quartz using ozone plasma or other bonding techniques. On each microfluidic channel 14, at least one pair of interdigitated transducers or electrodes (IDTs) 48 are located on opposing sides of the microfluidic channel 14.

FIG. 5 illustrates an embodiment in which there is a first pair of IDTs 48 and a second pair of IDTs 50 that is located across the microfluidic channel 14. The first pair of IDTs 48 is located at an upstream region along the microfluidic channel 14 while the second pair of IDTs 50 is located at a downstream region along the microfluidic channel 14 (fluid flows in direction of arrows A). In this embodiment, the first pair of IDTs 48 is used to focus the cells 100 in a particular lateral position within the microfluidic channel 14 while the second pair of IDTs 50 is used is used to temporarily permeabilize cells 100 via acoustic waves generated within the microfluidic channel 14. For example, the first pair of IDTs 48 may keep the cells 100 away from the walls of the microfluidic channel 14 to prevent fouling. The permeabilized cells 100 are able to receive biomolecular cargo 44 located in the surrounding fluid medium of the cells 100. The biomolecular cargo 44 in this embodiment flow with the cells 100 in the microfluidic channel 14. In some embodiments, the biomolecular cargo 44 may be focused along with the cells 100 so as to increase the proximity and physical interaction between the biomolecular cargo 44 and the cells 100.

Figure 13:
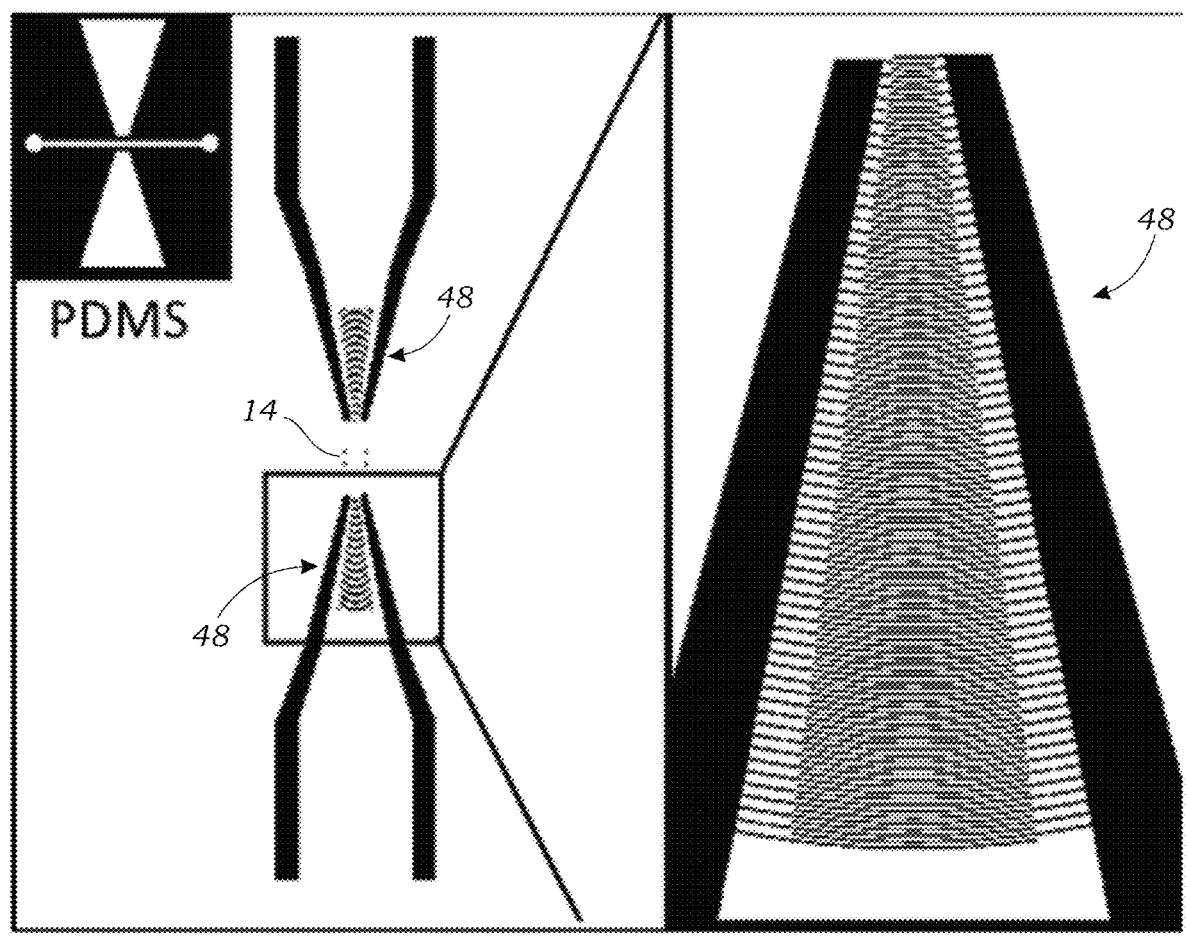
FIG. 13 illustrates a top down (left) and enlarged views of an IDT electrode having a curved or arced configuration.

The IDTs 48, 50 may be formed by photolithographic patterning onto the piezoelectric substrate 46 or other approaches to those skilled in the art. In photolithographic patterning the piezoelectric substrate 46 is coated inside a clean room with a photoresist (SFR 700-1.2, Dow) at 500 RPM for 5 seconds and 4500 RPM for 30 seconds. The photoresist coated LiNbO$_3$ wafers were then heated for 90 seconds at 90° C. and were exposed to ultraviolet radiation for 6.5 seconds at a power setting of 8.5 W using a Karl Suss contact aligner (MA/BA 6, Suss MicroTech) and a custom designed photomask (PhotomaskPortal). The photomask set the dimensions for the IDTs 48, 50 and was designed to have curved electrodes with a spacing of 10 µm between each. Furthermore, the dimensions of each electrode were set to be 1000 µm-200 µm×10 µm×40 mm which could generate a surface acoustic wave in a frequency range of 100 MHz. FIG. 13 illustrates a view of the IDT 48 with curved electrodes. The curved or arced electrode configuration is advantageous because it results in constructive interference of the SAWs generated in the microfluidic device 12. After exposure, devices were heated for 90 seconds at 110° C. and then developed in MF-26A developer (Dow) for 30 seconds. Electrodes were then formed by evaporating 10 nm of titanium and 30 nm of gold using an electron beam evaporator (CHA Solution). The photoresist and excess metal was then lifted off from the wafer by sonication in acetone for 15 minutes followed by sonication in isopropanol and deionized water for 1 minute, respectively.

The IDTs 48, 50 are electrically conductive and have a comb-like or interdigitated finger structure. The finger spacing help define the operating frequency of the IDTs 48, 50. The IDTs 48, 50 include electrical contacts where an alternating AC signal is applied using a separate signal generator 32 such as that disclosed in the embodiments of FIGS. 1, 2, 3A-3C, 4A, 4B. The signal generator 32 includes the ability to adjust the frequency(/ies) and amplitude(s) of the applied AC signal as described herein. Generally, signal generator 32 applies frequencies within the range of about 20 MHz to about 40 MHz, although in other constuctions different frequencies may still be employed that produce resonant harmonics within the microfluidic channel 14. The amplified signal that is applied to the IDTs 48, 50 may vary but a typical voltage that is applied is about 40V (peak-to-peak or 40V$_{p-p}$). At voltage levels above this, heat is generated in the microfluidic device 12 and may require one or more active cooling solutions to maintain the integrity of the microfluidic device 12. Lower voltage levels may result in reduced transfection efficiencies but may still be employed.

In one particular embodiment, a first AC signal or signal range is applied to the first pair of IDTs 48 while a second AC signal or signal range is applied to the second pair of IDTs 50. For example, a first channel of the signal generator 32 applies AC signals to the focusing IDTs 48 while a second channel of the signal generator 32 applies the AC signals to the permeabilizing IDTs 50. In this regard, both the focusing IDTs and the permeabilizing IDTs are powered concurrently.

For the first (i.e., focusing) stage that is formed by the first pair of IDTs 48, the pair of IDTs 48 are separated from each other by a distance that is approximately half a wavelength. The first stage of the system acts to focus the cells 100 into a tight column down the center of the microfluidic channel 14. The interference pattern achieved by this geometry and driving frequency(/ies) results in a pressure node located near the center of the microfluidic channel 14 efficiently funneling and focusing the cells 100 into a tight column.

For the second (i.e., permeabilizing) stage that is formed by the second pair of IDTs 50, the pairs of IDTs 50 are driven at a frequency(/ies) and amplitude(s) that are optimized for cell permeabilization. The particular frequency and amplitude can be adjusted or tuned based on the particular type of cell 100 in order to maximize payload delivery of biomolecular cargo 44 and maintain cell viability. As noted herein, the applied frequency to for IDTs 50 for permeabilization generally falls within the range of about 20 MHz to about 40 MHz. In some embodiments, the biomolecular cargo 40 may be co-flowed within the microfluidic channel 14 along with the cells 100. Alternatively, the biomolecular cargo 40 may be flowed sequentially such as that described herein in the context of the plasmid 40 embodiments illustrated in FIGS. 3A-3C where an inner surface of the microfluidic channel 14 is functionalized and plasmids 40 are adhered or tethered thereto by electrostatic attractive forces, followed by transfection.

Figure 6:
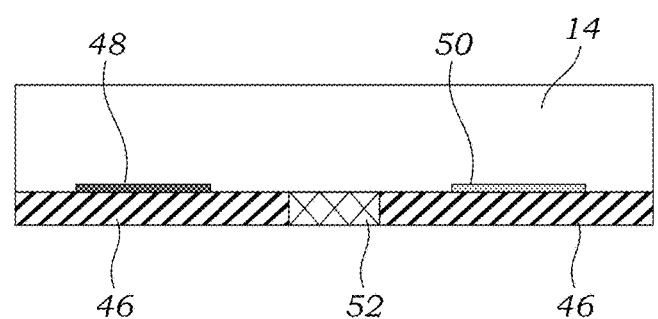
FIG. 6 is a cross-sectional view of the microfluidic device of FIG. 5 taken along the line A-A'.
Figure 7:
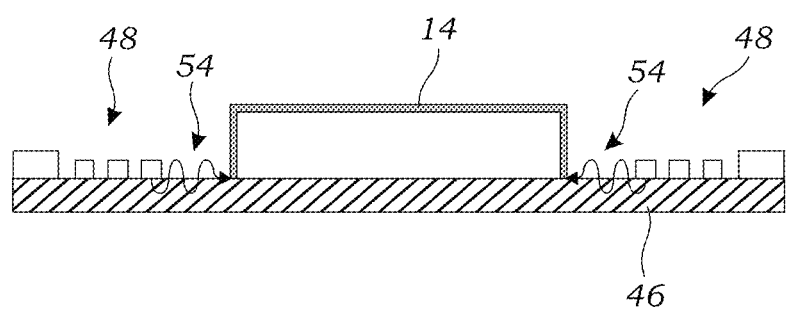
FIG. 7 is a cross-sectional view of the microfluidic device of FIG. 5 taken along the line B-B'.

As seen in FIG. 5, the first pair of IDTs 48 and the second pair of IDTs 50 can be separated via an acoustic damper 52 that is designed to minimize crosstalk between the focusing stage and the permeabilization stage. In one aspect, the acoustic damper 52 is a change in material or physical separation that is introduced in the piezoelectric substrate 46. For example, the first pair of IDTs 48 and the second pair of IDTs 50 can be separated using silicon as the acoustic damper 52 as illustrated in FIGS. 5 and 6. In other embodiments, the acoustic damper 52 may be omitted entirely. FIG. 7 illustrates another cross sectional view of the embodiment of FIG. 5 showing a cross-sectional view that passes through the first pair of IDTs 48. SAW waves 54 generated by the piezoelectric substrate 46 are also illustrated.

Figure 8:
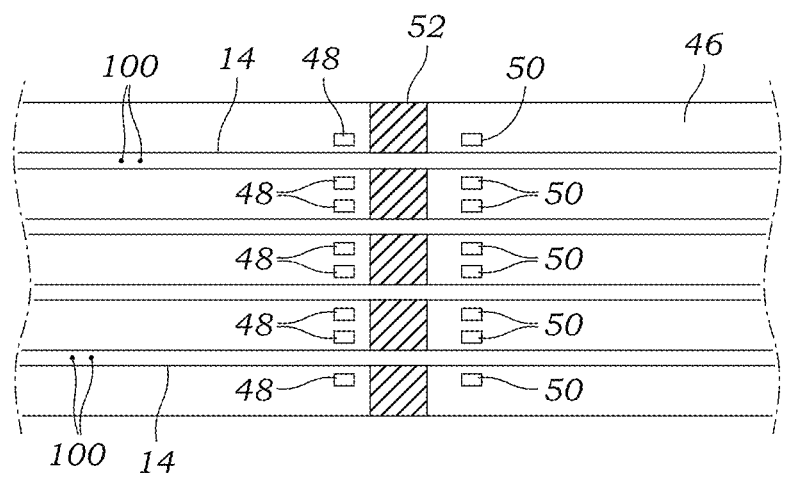
FIG. 8 is another embodiment of a system for the intracellular delivery of biomolecular cargo to living cells.

FIG. 8 illustrates an alternative embodiment of a microfluidic device 12 for the intracellular delivery of biomolecular cargo 44 to living cells 100 via vibrational cell deformability. In this embodiment, there are a plurality of microfluidic channels 14 are formed on or over a piezoelectric substrate 46. Like the embodiment of FIG. 5, there are first pairs of IDTs 48 that are located across the microfluidic channels 14 on an upstream region of the microfluidic channels 14. There are also illustrated second pairs of IDTs 50 that are located across the microfluidic channels 14 on a downstream region of the microfluidic channels 14. An acoustic damper 52 is illustrated that separates the first pairs of IDTs 48 and the second pairs of IDTs 50. This embodiment allows the processing of large numbers of cells 100 because the large numbers of microfluidic channels 14. While FIG. 8 illustrates both upstream and downstream IDTs 48, 50, in other embodiments only single pair of opposing IDTs 48 may be used. The acoustic damper 52 would also not be used in this alternative embodiment.

Figure 9:
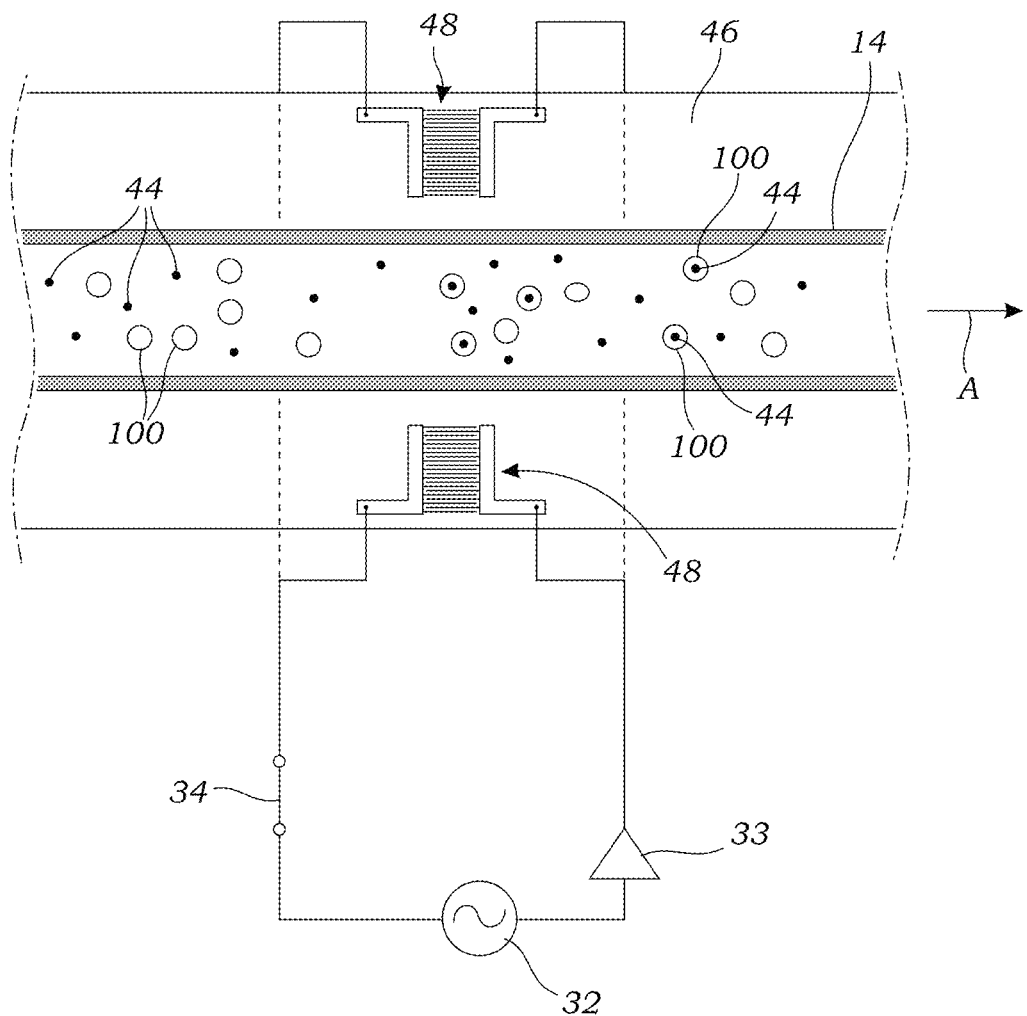
FIG. 9 illustrates another embodiment of a system for the intracellular delivery of biomolecular cargo to living cells.

FIG. 9 illustrates still another embodiment of a microfluidic device 12 for the intracellular delivery of biomolecular cargo 44 to living cells 100 via vibrational cell deformability. This embodiment is similar to that of FIGS. 5 and 6 except that there is a single pair of IDTs 48 disposed across the microfluidic channel 14. That is to say, there are no separate upstream focusing pairs of electrodes required in this embodiment. A single pair of IDTs 48 is able to permeabilize the cells 100 that pass through the microfluidic channel 14 in the region between the two IDTs 48. As seen in FIG. 9, the signal generator 32 is used to drive both pairs of IDTs 48 using amplifier 33. The signal generator 32 may be turned on/off using switch 34 or other switching circuitry. FIG. 9 illustrates fluid flowing down the microfluidic channel 14 in the direction of arrow A. As cells 100 pass the region of the microfluidic channel 14 located between the IDTs 48, the cells 100 are temporarily permeabilized whereby biomolecular cargo 44 enter the interior of the cells 100 as illustrated in FIG. 9.

As explained herein, the biomolecular cargo 40 may be freely floating in the fluid containing the cells 100 or, alternatively, the biomolecular cargo 40 may be bound to a vector 40 that aids in the delivery of the biomolecular cargo 40 into the cells 100. The transfection of the cells 100 may occur due to squeezing of the cells 100 within the microfluidic channel 14 caused by the SAWs. Alternatively, the transfection of the cells 100 may occur due to shearing the cells 100 along one or more inner surfaces 36 of the microfluidic channel 14 (or a combination of both squeezing and shear forces). For example, a vector 40 such as plasmid may be bound to an inner surface of the microfluidic channel 14 functionalized with APTES as explained herein. A shearing force may be applied to the cells 100 by the IDTs 48 to push the cells 100 against the inner surfaces 36 of the microfluidic channel 14 to promote transfection of the cells 100. In other embodiments, it may be advantageous to keep the cells 100 away from the walls of the microfluidic channel 14 (e.g., to prevent fouling) and acoustic focusing using IDTs 48 can be used for this purpose.

Figure 10:
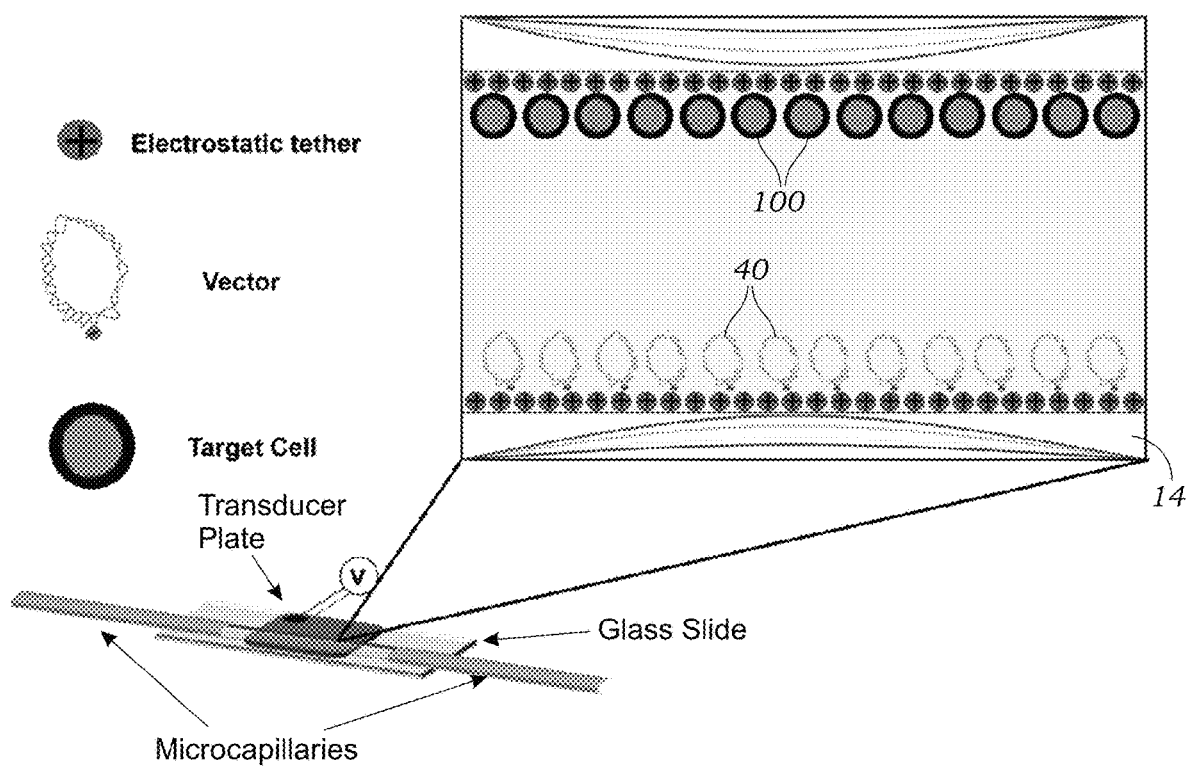
FIG. 10 illustrates a microcapillary-based microfluidic device used for experimentation as described herein.

To test the ability of a microfluidic devices 12 described herein to deliver biomolecular cargo to the interior of cells, a microfluidic device was formed by bonding silanized glass microcapillaries (VitroCom, Mountain Lakes, N.J.) to a zirconate titanate (PZT) transducer plate (STEMiNC, Doral, Fla.) and a glass slide as a supporting frame to protect the microfluidics in the system. FIG. 10 illustrates the experimental microcapillary-based microfluidic device. The microcapillaries were square glass microcapillaries having internal dimensions of 80 μm×80 μm and served as the microfluidic channel. The microcapillary was cleaned by carefully dipping ends in solution containing 3:1 concentrated sulfuric acid and 30% hydrogen peroxide for 30 min. This cleaning step removes organic molecules while adding hydroxyl functionalities to the glass surface. Next, the microcapillaries were rinsed and sonicated in 18-MΩ deionized water (Millipore) for five (5) cycles of five (5) minutes and placed in a drying oven at 110° C. for 6 hours. The dried microcapillaries were then dipped into a 5% (v/v) ethanolic solution of (3-Aminopropyl)triethoxysilane (APTES, Sigma Aldrich) and placed in an oven at 60° C. for five (5) minutes. This was followed by three (3) cycles of sonication in ethanol for five (5) minutes to remove any passively adsorbed APTES molecules. The microcapillaries were stored in ethanol until device assembly.

The glass slides were cut into long strips that were the width of the transducer plate. The transducer plate is mounted onto the slide with a thin layer of Devcon 5-minute epoxy (300007-392, VWR) after soldering 30-gauge wire to the front and back of the PZT plates. A thin layer of optical adhesive (NOA 61, Norland Products, Inc.) was then added to the surface of the plate using a razor blade and the silanized glass microcapillaries were mounted to the adhesive and cured under an ultraviolet lamp for five (5) minutes. Polyethylene tubing (PE 50, Instech Laboratories, Inc., Plymouth Meeting, Pa.) was then placed on both ends of the microcapillary and sealed with small drops of epoxy. After drying, the tubing was secured to the glass slide with double sided tape and tested for leaks by running ethanol through the device. The resonance frequencies for each completed microfluidic device were checked using a vector network analyzer (VNA-120, Array Solutions, Sunnyvale, Tex.) and were found to be in the range of 1-10 MHz.

For the microfluidic device that included IDTs such as those illustrated in FIGS. 5, 6, 7, and 9, interdigitated electrodes (IDTs) were photolithographically patterned onto wafers of lithium niobate ($LiNbO_3$) to generate a surface acoustic wave in a frequency range of 20 MHz to 40 MHz. Microfluidic polydimethylsiloxane (PDMS, Sigma Aldrich) channels were formed by pouring the PDMS over a predefined silicon mould that has features that are 3 cm×150 μm×80 μm. The PDMS microfluidic channels were then cured overnight and cut from the silicon wafer. The channels were then sealed to the $LiNbO_3$ by oxidizing both the wafer and the PDMS surface with an oxygen plasma cleaner (PD-32G, Harrick) at a low RF frequency for one (1) minute. This plasma cleaning step allowed the formation of hydroxyl functionalities to form on the surface of both the $LiNbO_3$ and PDMS. The PDMS microchannel was then placed equidistantly between the IDTs on the $LiNbO_3$ wafer and was covalently sealed together through a condensation reaction by heating in an oven at 60° C. overnight. Resonance frequencies for the $LiNbO_3$ devices were similarly checked with the VNA-120.

For imaging purposes, the fabricated PZT devices (microcapillary-based and IDT-based) were vertically aligned in a custom-built microscope stage so that the cross section of the microfluidic channel was in the optical path of a microscope. The tubing was then connected to a syringe using by a simple insertion of a 23-gauge needle and the flow rate was controlled with a syringe pump (Fusion 4000, Chemyx, Inc., Stafford, Tex.). Transducers were stimulated using a signal generator (81150A, Agilent) connected to a broadband amplifier (25A250B 25 Watt CW, 10 kHz-250 MHz power amplifier, AR Products, Souderton, Pa.), which output a sinusoidal wave at the desired resonance frequency of the device with an amplitude of 40 $V_{p-p}$. The $LiNbO_3$ devices operated with the same experimental parameters but were imaged directly without the custom stage.

For the microcapillary-based device, plasmids containing green fluorescent protein were loaded into the microcapillaries for transfection. As explained herein, the plasmids (which are negatively charged) are adhered or tethered to the positively charged, silanized interior surface of the microcapillaries. Green fluorescent protein expressing plasmid (V88320, ThermoFischer) was flowed into the microcapillary at a flow rate of 3.33 μL/min with a concentration of 50 μg/μL for thirty (30) minutes. This allows the plasmid to diffuse in the microcapillary and tether electrostatically to the positively charged APTES-functionalized surface due to the native negative charge of the plasmid. This was followed by a wash step with 1× phosphate buffer saline solution (Gibco) to remove free floating plasmid from solution. For tests involving both free floating and tethered plasmid, concentrations were varied over a range of 10-1000 ng/μL in solutions containing both RPMI 1640 (Gibco) cell media and Jurkat Cells (TIB152, ATCC). These cells were concentrated to 3 million cells/mL and introduced into the microcapillary at flow rates ranging from 100-1,000 μL/min. The signal generator was set to output a frequency in the ranges of 3 MHz-4 MHz (depending on the network analyzer measurement for resonance) for cell shearing or 9.5 MHz-10 MHz for cell squeezing. As a control, cells were introduced into the microcapillary device in the same experimental conditions without an acoustic wave being applied.

Figure 11A:
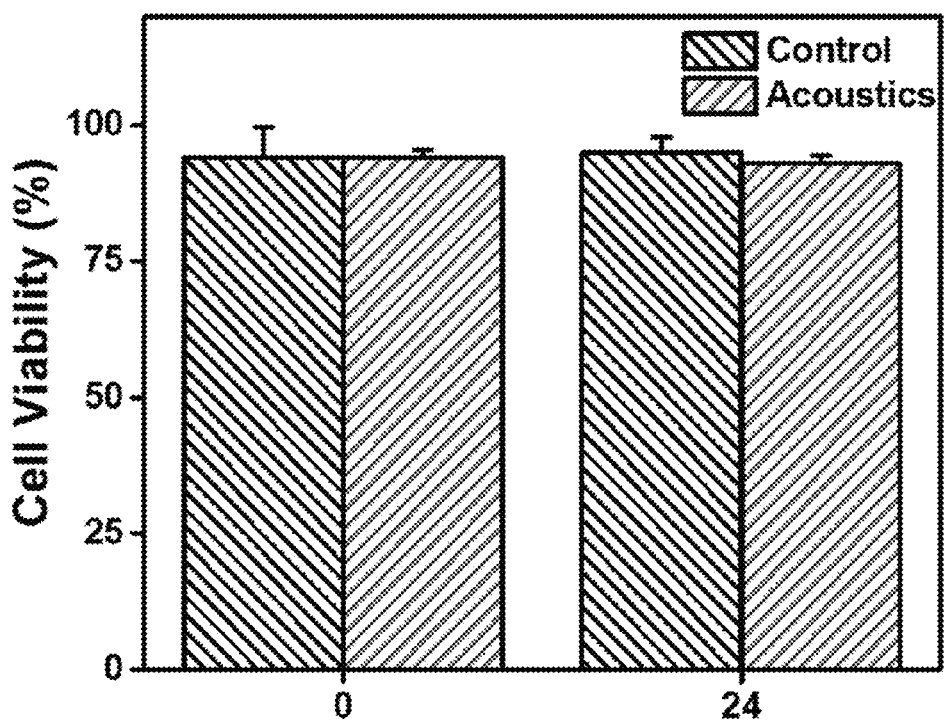
FIG. 11A illustrates a graph showing cell viability percentage for Jurkat cells at times 0, and 24 hours after generation of BAWs within the microcapillary-based device.
Figure 11B:
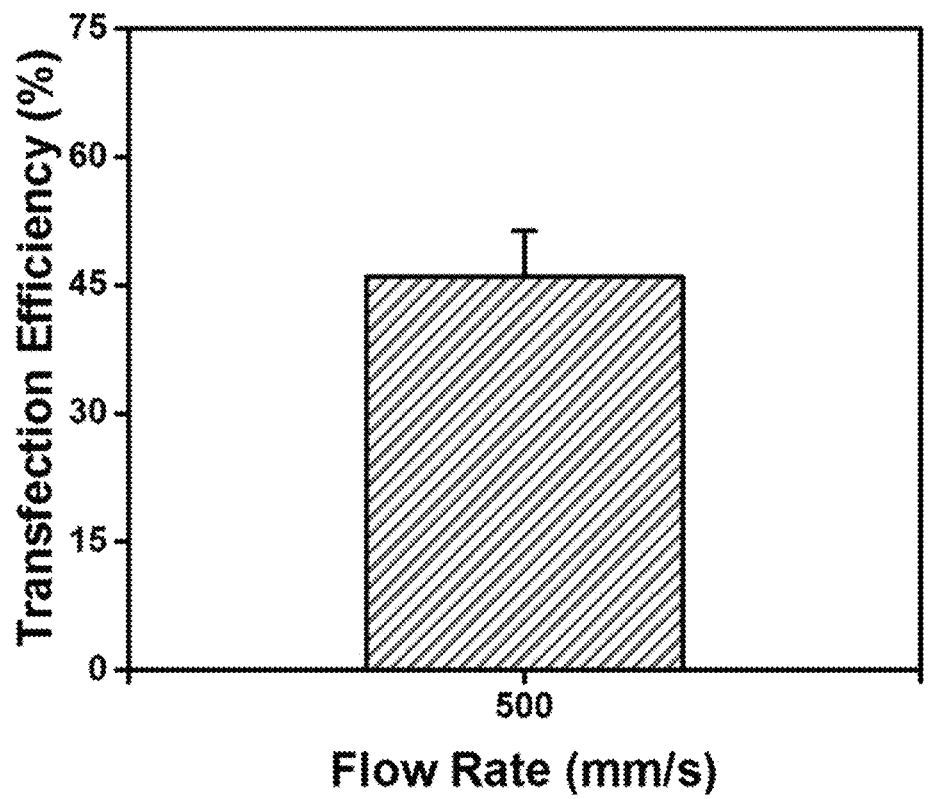
FIG. 11B illustrates a graph of the transfection efficiency of Jurkat cells with green fluorescent protein (GFP) expression plasmids that were tethered to the inner surface of the microcapillary in response to applied vibrational energy.

FIG. 11A illustrates a graph showing cell viability percentage for Jurkat cells at times 0, and 24 hours after generation of BAWs within the microcapillary-based device. As seen in FIG. 11A, cell viability was maintained after application of the vibrational energy to the cells. FIG. 11B illustrates the transfection efficiency of cells with green fluorescent protein (GFP) expression plasmids that were tethered to the inner surface of the microcapillary in response to applied vibrational energy to induce cell shearing against the inner surface of the microcapillary. As seen in FIG. 11B, a transfection efficiency (i.e., number of transfected cells divided by the total number of processed cells) was around 45%.

In one particular embodiment, a microfluidic device 12 or multiple devices 12 connected together may include a plurality of microfluidic channels that could prepare all the cells necessary for a gene-modified hematopoietic stem cell transplant for a 12 kg infant in one (1) hour. This estimate assumes processing of 50,000 cells per sec per microfluidic channel. This time compares favorably to current electroporation methods that require many hours and significant additional processing steps. In such a method, the patient's own cells may be run through the device and subject to permability inducing acoustic waves so that genes can be modified with a targeted endonuclease gene editing system such as CRISPR/Cas9 in combination with guide nucleic acids as described above.

Figure 12:
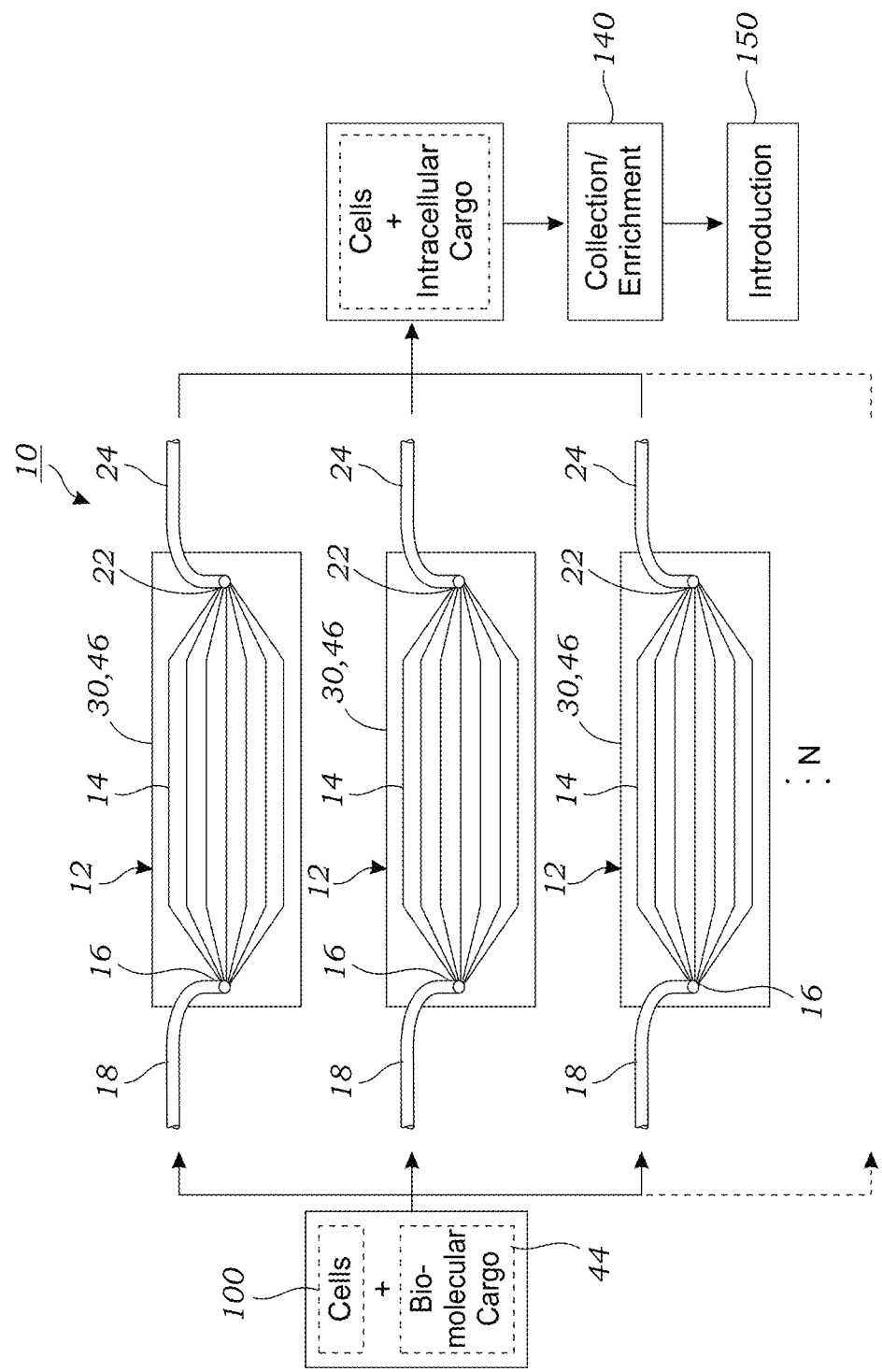
FIG. 12 illustrates a schematic representation of a microfluidic-based system for the intracellular transport biomolecular cargo into live cells.

FIG. 12 illustrates a schematic representation of a microfluidic-based system 10 for the intracellular transport biomolecular cargo 44 into cells 100. As seen in FIG. 12, the cells 100 and biomolecular cargo 44 are run through one or more microfluidic devices 12. In this particular embodiment, a plurality of microfluidic devices 12 (N is the total number of microfluidic devices 12) are employed in parallel so that large numbers of cells 100 may be processed. As explained herein, according to one preferred embodiment of the invention, flow rates that achieve processing rates of cells 100 between about 50 and about 100,000 cells/sec/microfluidic channel may be achieved.

The cells 100 may be obtained from a subject, for example, a human. The cells 100 may include, as one example, stem cells or cells with stem-like properties that are obtained for example, from the bone marrow of a subject. In one preferred embodiment, the cells 100 are living cells and remain living after intracellular delivery of biomolecular cargo 44. The cells 100 may also include immune cells that are obtained from a subject. An example includes T-lymphocytes that are obtained from the subject for adoptive cellular therapies. The invention is not, however, limited to use with stem cells or immune cells. In other embodiments, healthy cells 100 may also be run through the system 10. As noted herein, the cells 100 are run through the microfluidic device(s) 12 along with the biomolecular cargo 44 that are to be intracellularly transported into the cells 100. In still another embodiment, the cells 100 may be obtained from a culture or the like. For example, bacteria cells 100 or enveloped viruses may be grown in culture and then processed. Of course, bacterial cells 100 or enveloped viruses may also be obtained from a subject.

The permeabilized cells 100 that uptake the biomolecular cargo 44 in response to the applied vibrational energy are then captured or collected after passing through the microfluidic devices 12. This is illustrated in operation 140 in FIG. 10. For example, the outlets 22 may be coupled to a collection container (not shown) or other receptacle (e.g., bag, vial(s), bottle(s) which may be used to enrich the concentration of collected cells 100 that are processed using the system 10. In one embodiment, for example, where the biomolecular cargo 44 include gene-modification components, the collected cells 100 that have been modified genetically may then be introduced into a subject as seen in operation 150. The subject that receives the processed cells 100 may be the same individual that provided the cells 100 that were initially processed with the system 10. Alternatively, the recipient of the cells 100 may be a different subject from the source of cells 100 that are run through the system 10.

The disclosed method circumvents the limitations of sonoporation (e.g., low efficiency, increased risk of cell death, low throughput) by modifying and deforming the target cells gently, without the need for cavitation as they flow through a microfluidic network. By varying parameters such as the frequency(/ies) and amplitude(s) of the surface acoustic wave(s), one can tailor the mechanical and physical characteristics of the local cellular microenvironment to preferentially influence cellular behavior. The method can also be made highly parallel to increase throughput.

While embodiments of the present invention have been shown and described, various modifications may be made without departing from the scope of the present invention. As explained herein, the term "cells" encompasses eukaryotic and prokaryotic cells. Further, enveloped viruses may be transfected just as the cells described herein. Thus, all embodiments described herein that apply to cells equally apply to enveloped viruses. The invention, therefore, should not be limited, except to the following claims, and their equivalents.

What is claimed is:

1. A microfluidic device for the intracellular delivery of biomolecular cargo into cells or enveloped viruses comprising:
    a piezoelectric substrate;
    a microfluidic substrate disposed on the piezoelectric substrate and having one or more microfluidic channels disposed therein and fluidically coupled to a solution containing cells or enveloped viruses, wherein the one or more microfluidic channels contain one or more inner surfaces coated with plasmids containing the biomolecular cargo;
    a pump configured to pump the solution containing the cells or enveloped viruses into the one or more microfluidic channels; and
    a signal generator coupled to the piezoelectric substrate, wherein the piezoelectric substrate, when actuated, generates bulk acoustic waves (BAWs) that move the cells or enveloped viruses against the one or more inner surfaces coated with plasmids containing the biomolecular cargo and causes permeabilization of the cells or enveloped viruses which effectuates transfection of the cells or enveloped viruses.

2. The microfluidic device of claim 1, wherein the one or more inner surface comprises a chemically functionalized surface.

3. The microfluidic device of claim 2, wherein the chemically functionalized surface comprises a self-assembled monolayer.

4. The microfluidic device of claim 1, wherein the one or more inner surface comprises a silanized surface.

5. The microfluidic device of claim 1, wherein the biomolecular cargo comprises one or more of interfering RNA, proteins, transcription factors, or nuclease gene-editing molecules or transcription activator-like effector nucleases, or combinations thereof.

6. The microfluidic device of claim 1, wherein the biomolecular cargo comprises one or more of Cas9 protein, Cas9 mRNA, associated guide RNA sequences, and homologous donor template nucleic acids, or combinations thereof.

7. A method of using the microfluidic device of claim 1, comprising:
flowing a solution containing the cells or enveloped viruses with the pump through the one or more microfluidic channels; and
actuating the piezoelectric substrate with the signal generator while the solution containing the cells or enveloped viruses passes through the one or more microfluidic channels adjacent to the piezoelectric substrate.

8. The method of claim 7, wherein the cells comprise eukaryotic cells or prokaryotic cells.

9. A method of using the microfluidic device of claim 1, comprising:
flowing a first solution including the plasmids containing the biomolecular cargo through the one or more microfluidic channels, wherein the plasmids containing the biomolecular cargo adheres to one or more inner surfaces of the one or more microfluidic channels;
flowing a second solution containing the cells or enveloped viruses through the one or more microfluidic channels; and
actuating the piezoelectric substrate with the signal generator while the solution containing the cells or enveloped viruses passes through the one or more microfluidic channels adjacent to the piezoelectric substrate.

10. The method of claim 9, wherein the cells comprise eukaryotic cells or prokaryotic cells.

11. A microfluidic device for the intracellular delivery of biomolecular cargo into cells or enveloped viruses comprising:
a piezoelectric substrate having a microfluidic channel disposed on a surface thereof and fluidically coupled to a solution containing cells or enveloped viruses;
a pump configured to pump the solution containing the cells or enveloped viruses into an inlet of the microfluidic channel;
a first pair of interdigitated electrodes (IDTs) disposed on opposing sides of the microfluidic channel at a first location along the microfluidic channel;
a second pair of interdigitated electrodes (IDTs) disposed on opposing sides of the microfluidic channel at a second location along the microfluidic channel, the second location being located downstream of the first location;
a signal generator configured to apply an AC voltage to the first pair of IDTs and when actuated generates bulk acoustic waves (BAWs) that focus the cells or enveloped viruses at a lateral position of the microfluidic channel and configured to apply an AC voltage to the second pair of IDTs and when actuated causes permeabilization of the cells or enveloped viruses which effectuates transfection of the cells or enveloped viruses.

12. The microfluidic device of claim 11, wherein the piezoelectric substrate comprises one of lead zirconate titanate, lithium niobate, or quartz.

13. The microfluidic device of claim 11, further comprising an acoustic damper interposed between the first pair of interdigitated electrodes (IDTs) and the second pair of interdigitated electrodes (IDTs).

14. The microfluidic device of claim 13, wherein the acoustic damper separates the piezoelectric substrate into separate substrates.

15. The microfluidic device of claim 13, wherein the acoustic damper extends generally orthogonally with respect to the microfluidic channel.

16. A microfluidic device for the intracellular delivery of biomolecular cargo into cells or enveloped viruses comprising:
a piezoelectric substrate having a plurality of microfluidic channels disposed on a surface thereof, the plurality of microfluidic channels fluidically coupled to a solution containing cells or enveloped viruses;
a pump configured to pump the solution containing the cells or enveloped viruses into the plurality of microfluidic channels;
a first plurality of respective pairs of interdigitated electrodes (IDTs) disposed on opposing sides each of the plurality of microfluidic channels at a first location along the plurality of microfluidic channels;
a second plurality of respective pairs of interdigitated electrodes (IDTs) disposed on opposing sides of each of the plurality of microfluidic channels at a second location along the plurality of microfluidic channels, the second location being located downstream of the first location;
a signal generator configured to apply an AC voltage to the first plurality of respective pairs of interdigitated electrodes (IDTs) and the second plurality of respective pairs of interdigitated electrodes (IDTs), wherein actuation of the first plurality of respective pairs of IDTs focuses the cells or enveloped viruses at a lateral location within the plurality of microfluidic channels and wherein actuation of the second plurality of respective pairs of IDTs causes permeabilization of the cells or enveloped viruses which effectuates transfection of the cells or enveloped viruses.

17. The microfluidic device of claim 16, wherein the piezoelectric substrate comprises one of lead zirconate titanate, lithium niobate, or quartz.

18. The microfluidic device of claim 16, further comprising an acoustic damper interposed between the first plurality of respective pairs of interdigitated electrodes (IDTs) and the second plurality of respective pairs of interdigitated electrodes (IDTs).

19. The microfluidic device of claim 18, wherein the acoustic damper separates the piezoelectric substrate into separate substrates.

20. The microfluidic device of claim 18, wherein the acoustic damper extends generally orthogonally with respect to the plurality of microfluidic channels.

21. A method of using the device of claim 11, comprising:
flowing the solution containing the cells or enveloped viruses through the microfluidic channel with the pump; and
applying a signal to the first pair of IDTs and the second pair of IDTs so as to permeabilize at least some of the cells or enveloped viruses, wherein the biomolecular cargo enters the interior of the permeabilized cells or enveloped viruses.

22. The method of claim 21, wherein the cells comprise eukaryotic cells or prokaryotic cells.

23. The method of claim 21, wherein the biomolecular cargo comprises one or more nucleic acid sequences.

24. The method of claim 21, wherein the first pair of interdigitated electrodes (IDTs) are driven at a driving frequency within the range of about 20 MHz to about 40 MHz.

25. The method of claim 21, wherein the biomolecular cargo comprises one or more of interfering RNA, proteins, transcription factors, or nuclease gene-editing molecules or transcription activator-like effector nucleases, or combinations thereof.

26. The method of claim 21, wherein the biomolecular cargo comprises one or more of Cas9 protein, Cas9 mRNA, associated guide RNA sequences, and homologous donor template nucleic acids, or combinations thereof.

* * * * *